United States Patent
Gilman

(10) Patent No.: US 11,253,687 B2
(45) Date of Patent: Feb. 22, 2022

(54) CLEANSING SWAB FOR NEEDLE PEN ASSEMBLY

(71) Applicant: Michael J. Gilman, Fayetteville, NY (US)

(72) Inventor: Michael J. Gilman, Fayetteville, NY (US)

( * ) Notice: Subject to any disclaimer, the term of this patent is extended or adjusted under 35 U.S.C. 154(b) by 312 days.

(21) Appl. No.: 16/035,149

(22) Filed: Jul. 13, 2018

(65) Prior Publication Data
US 2019/0298981 A1 Oct. 3, 2019

Related U.S. Application Data

(60) Provisional application No. 62/650,380, filed on Mar. 30, 2018.

(51) Int. Cl.
*A61M 5/32* (2006.01)
*A61F 13/40* (2006.01)
*A61F 13/38* (2006.01)

(52) U.S. Cl.
CPC .......... *A61M 35/006* (2013.01); *A61F 13/38* (2013.01); *A61M 5/3202* (2013.01); *A61M 5/3293* (2013.01)

(58) Field of Classification Search
CPC .............. A61M 35/006; A61M 5/3293; A61M 5/3202; A61M 39/16; A61M 35/003; A61M 2005/3117; A61M 39/162; A61M 5/24; A61F 13/38; A61F 13/36; A61F 11/006

See application file for complete search history.

(56) References Cited

U.S. PATENT DOCUMENTS

| | | | |
|---|---|---|---|
| 4,026,287 A | 5/1977 | Haller | |
| 4,507,117 A | 3/1985 | Vining | |
| 4,643,200 A | 2/1987 | Jennings, Jr. | |
| 4,650,468 A | 3/1987 | Jennings, Jr. | |
| 4,675,005 A | 6/1987 | DeLuccia | |
| 4,692,156 A | 9/1987 | Haller | |
| 4,710,170 A | 12/1987 | Haber et al. | |
| 4,747,830 A | 5/1988 | Gloyer et al. | |
| 4,790,822 A | 12/1988 | Haining | |
| 4,950,251 A | 8/1990 | Haining | |
| 5,112,316 A | 5/1992 | Venturini | |
| 5,147,328 A | 9/1992 | Dragosits et al. | |
| 5,244,465 A | 9/1993 | Michel | |
| 5,342,323 A | 8/1994 | Haining | |
| 5,941,857 A * | 8/1999 | Nguyen | A61M 5/3213 604/195 |

(Continued)

*Primary Examiner* — Nicholas J. Weiss
*Assistant Examiner* — Alessandro R Del Priore
(74) *Attorney, Agent, or Firm* — Barclay Damon LLP

(57) ABSTRACT

A needle cap assembly for use in combination with a needle pen comprising: (i) a needle cap having a needle cannula for injecting a fluid medication into an injection site, (ii) an internal cap configured to be disposed over an injection end of the needle cap, (iii) an external cap having a cavity configured to envelop the internal and needle caps, (iv) a sealing tab configured to seal a cavity of the external cap for enclosing or housing the needle cap assembly, and (v) a cleansing swab disposed in internally of the needle cap assembly. The cleansing swab is disposed internally of the needle cap and includes an absorptive material loaded with a cleansing fluid to clean an injection site prior to injection of fluid medication.

3 Claims, 5 Drawing Sheets

(56) References Cited

U.S. PATENT DOCUMENTS

| | | | | |
|---|---|---|---|---|
| 5,989,229 | A * | 11/1999 | Chiappetta | A61M 5/3202 604/1 |
| 7,393,345 | B2 * | 7/2008 | Yang | A61B 5/150694 604/198 |
| 8,883,499 | B2 | 11/2014 | Hedrick et al. | |
| 2009/0041619 | A1 | 2/2009 | Cady et al. | |
| 2009/0297400 | A1 | 12/2009 | Cady et al. | |
| 2011/0184382 | A1 | 7/2011 | Cady | |
| 2012/0111368 | A1 * | 5/2012 | Rahimy | A61M 39/20 134/22.1 |
| 2013/0053751 | A1 * | 2/2013 | Holtham | A61M 5/002 604/1 |
| 2015/0231289 | A1 * | 8/2015 | Webb | A61L 2/18 604/192 |
| 2016/0220762 | A1 * | 8/2016 | Goral | A61B 5/150305 |
| 2017/0027817 | A1 | 2/2017 | Thorne, Jr. et al. | |
| 2018/0296772 | A1 * | 10/2018 | Chu | A61M 5/3202 |
| 2019/0009074 | A1 * | 1/2019 | Drmanovic | A61J 1/2048 |

* cited by examiner

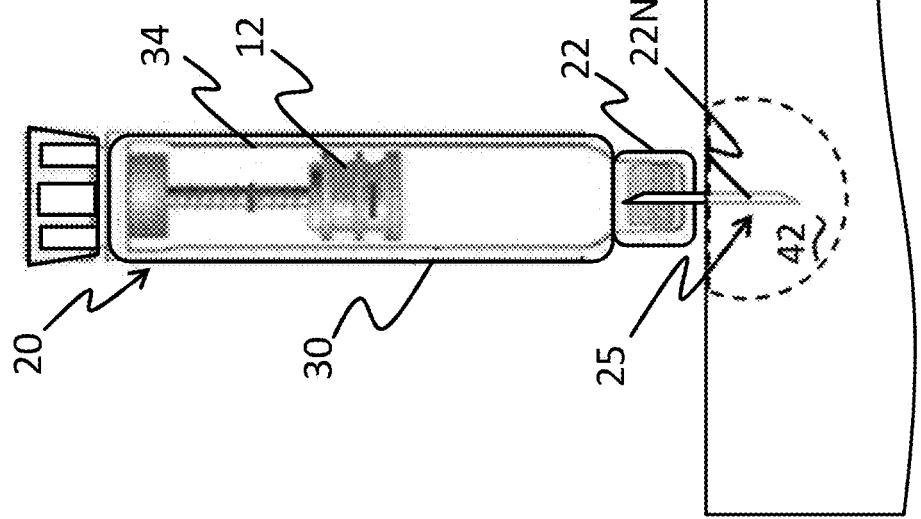
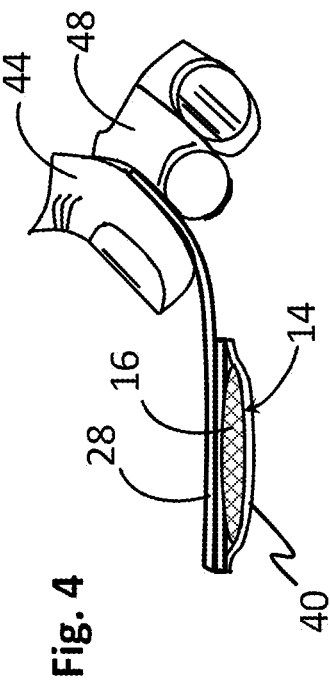
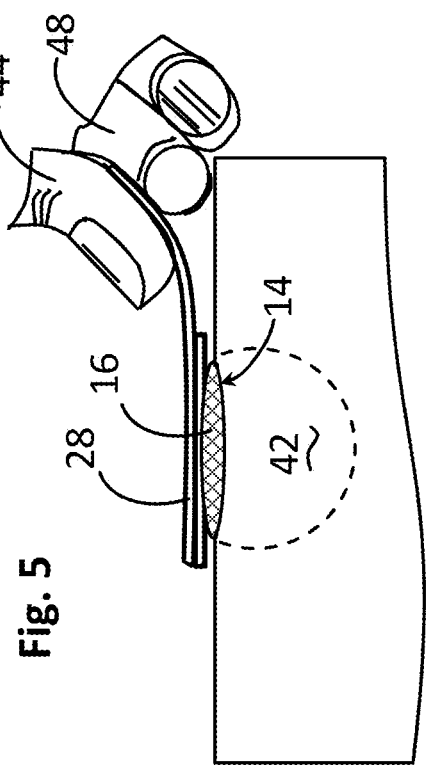

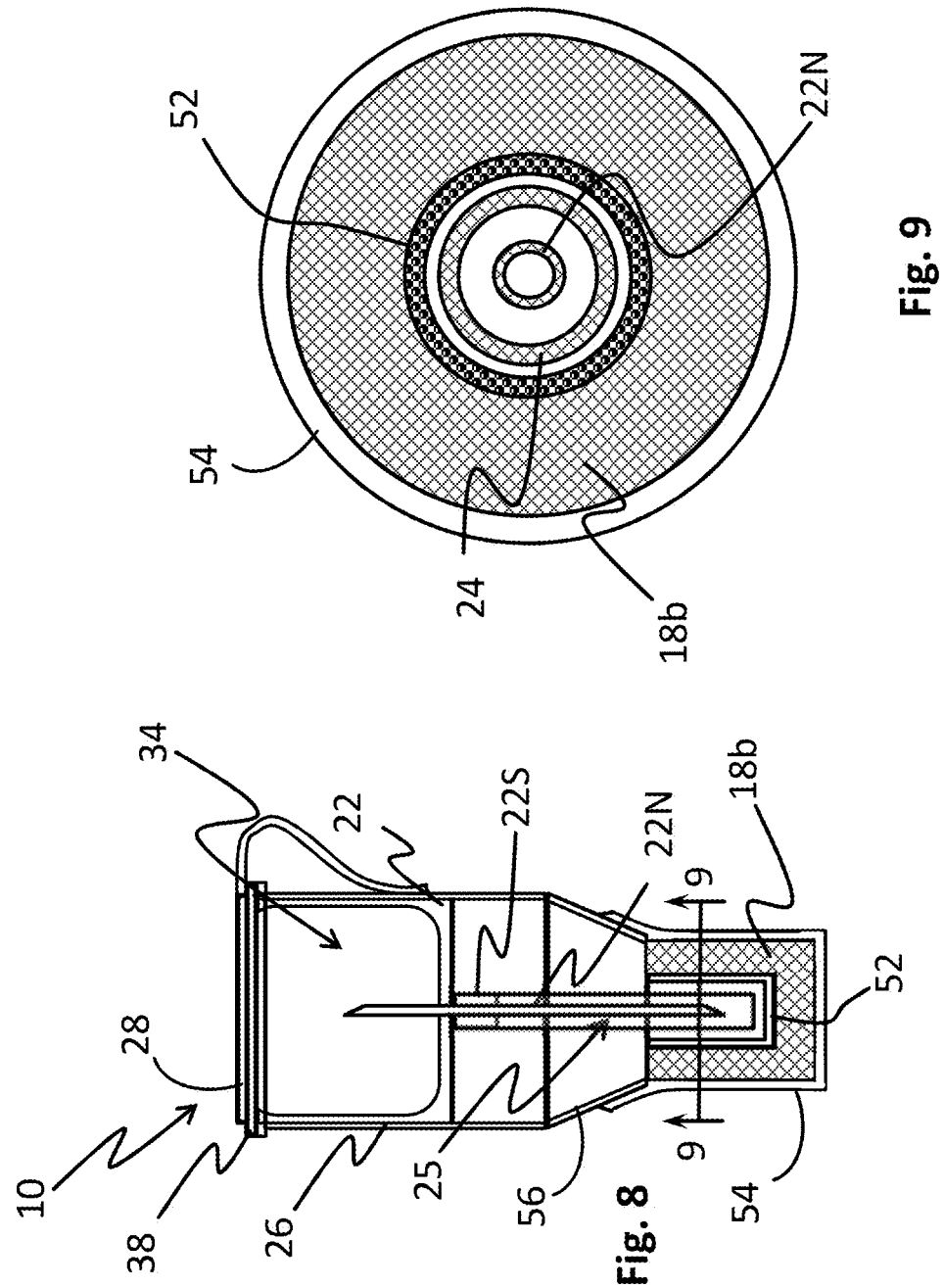

CLEANSING SWAB FOR NEEDLE PEN ASSEMBLY

RELATED APPLICATION

This application is a non-provisional of, and claims the benefit and priority of, U.S. Provisional Patent Application No. 62/650,380, filed on Mar. 30, 2018. The complete specification of such application is hereby incorporated by reference in its entirety.

BACKGROUND

The subject matter disclosed herein relates to cleansing swabs loaded with a cleansing fluid such as an alcohol-based cleansing fluid for disinfecting the site of a needle injection, and, more particularly, to a new and useful article and method for integrating a cleansing swab with a needle pen cap assembly to facilitate packaging, storage, handling and transport of such cleansing swabs prior to use.

Fluid medications, such as insulin for diabetes, fertility hormones, or antihistamines for allergies, are often self-administered by the affected patient. Such fluid medications generally replenish or reproduce enzymes/hormones which are not properly or appropriately being produced by one of the body's organs or glands. For example, needle pens are typically used to inject a fairly precise quantity of insulin to patients with diabetes to augment or replace a lack of insulin produced by the pancreas. Inasmuch as the level of insulin must be maintained at a fairly precise level, injections of insulin may be given several times in the course of a day. It will be appreciated, therefore, that an injection site, if used regularly, can become irritated or infected if not cared for properly.

Such fluid medications are typically integrated into a needle pen having a needle cannula in fluid communication with a vial of medication. As pressure is applied to the injection site, the body of the needle pen telescopes to apply pressure to a syringe plunger which injects the medication through the output end of the needle cannula.

As previous mentioned, a typical diabetes patient will require injections of insulin several times during the course of a single day. While the typical regiment for administration may be in the privacy of a patient's home, it is not uncommon for the fluid mediation to be administered in public locations, such as places of employment, restaurants, or during travel. With respect to the latter, it will be appreciated that such locations are not sterile and, as such, present an increased opportunity for the transmission of bacteria and/or other infectious disease. That is, there may be no opportunity to clean the site of the injection with a cleansing fluid such as with an alcohol, iodine or other liquid cleanser.

To facilitate the preparation and sterilization of the needle penetration site, manufacturers of the needle pens generally suggest that a user acquire a bottle of cleansing fluid, cotton swabs, and cleansing gauze for the purposes of preparation and sterilization of the injection site. Unfortunately, the user often forgets to include such additional materials/supplies when travelling with the needle pen/vials of medication. As such, the user will typically forego cleaning the site of penetration and risk contracting potentially harmful pathogens or a dangerous contagion.

A need, therefore, exists for a simple, sanitary article and method for cleaning an injection site prior to delivery of liquid medication, which article may be included with other items for administering medication injection and which method may be conducted without a need for planning, preparation, or a significant amount of forethought.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are, therefore, not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Differences between otherwise like parts may cause to those parts to be indicated with different numerals. Different parts are indicated with different numerals. Thus, for further understanding of the invention, reference can be made to the following detailed description, read in connection with the drawings in which:

FIG. 4 depicts a partially sectioned side view of one embodiment of the needle pen cap assembly wherein the sealing tab/cleansing swab is detached from the external cap of the needle pen cap assembly and wherein the cleansing packet/swab is disposed in combination with the underside/inside surface of the sealing tab.

FIG. 5 depicts a partially section side view of the sealing tab/cleansing swab being manipulated by the thumb and index finger of a user to sterilize an injection site.

FIG. 6 depicts a side view of the needle pen injecting a dose of fluid medication into the injection site.

FIG. 8 depicts a sectioned side view of yet another embodiment of the needle pen cap assembly wherein a cleansing swab is disposed in combination with an end portion of the needle pen cap assembly and a sealing member is disposed over the cleansing swab to form a fluid tight seal with an intermediate portion of the needle pen cap assembly.

FIG. 9 depicts a cross-sectional view taken substantially along line 9-9 of FIG. 8.

SUMMARY OF THE DISCLOSURE

A needle cap assembly is provided for use in combination with a needle pen comprising: (i) a needle cap having a needle cannula for injecting a fluid medication into an injection site, (ii) an internal cap configured to be disposed over an injection end of the needle cap, (iii) an end cap having a cavity configured to envelop the internal and needle caps, (iv) a sealing tab configured to seal a cavity of the external cap for enclosing or housing the needle cap assembly, and (v) a cleansing swab disposed in internally of the needle cap assembly. The cleansing swab includes an absorptive material loaded with a cleansing fluid to clean an injection site prior to injection of fluid medication.

DETAILED DESCRIPTION

The present disclosure is directed to an article and method for preparing an injection site prior to delivery of a liquid medication, and, more particularly, to an article and method for preparing an injection site prior to and/or, for receipt of, a liquid medication by a needle pen. The needle pen includes a container for storing a vial, or supply of, liquid medication such as insulin, antihistamines, blood thinners, hormones etc. As mentioned in the Background of the disclosure, such liquid medications generally replenish/reproduce enzymes/hormones which are not properly, or appropriately, produced by an organ or gland of the body. Furthermore, there is a regular need to sterilize, or clean the site of an injection to prevent the spread of a potentially harmful bacteria or virus.

Figure 1:
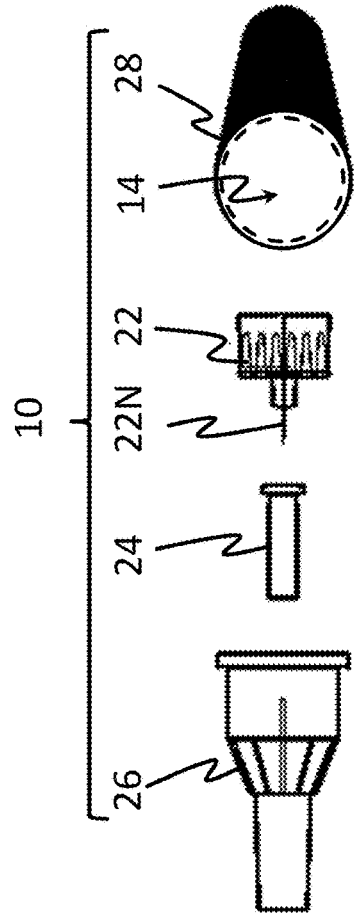
FIG. 1 is an exploded view of a needle pen cap assembly including a needle cannula disposed through a needle cap, an internal cap configured to be disposed over the injection end of the needle cannula, an external cap configured to envelope the internal cap and an outwardly-facing surface of the needle cap, and a sealing tab/cleansing swab adhesively bonded to the open end of the needle cap such that the cleansing swab is disposed internally of the needle cap assembly.
Figure 2:
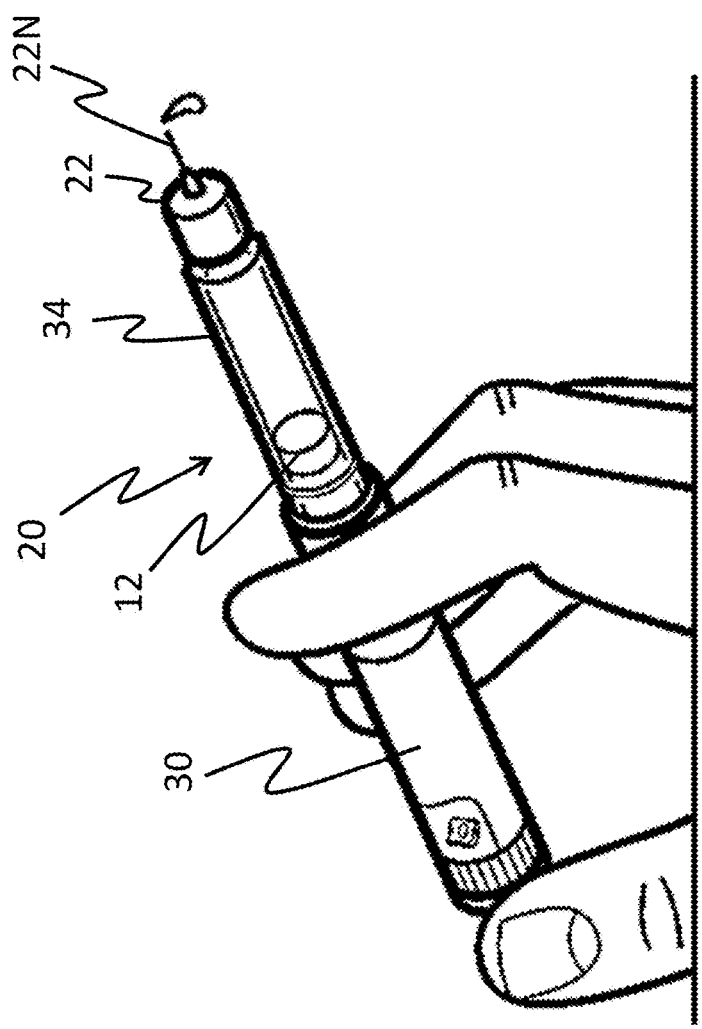
FIG. 2 is a perspective view of a needle pen being manipulated prior to injecting a dose of fluid medication.

FIGS. 1 and 2 depict a new and useful needle pen cap assembly 10 for use in combination with a needle pen 20. The needle pen cap assembly 10 will generally be fabricated/sold as a sterile unit for integration with a needle pen body 30 which includes a plunger 12 for pressurizing a vial (not shown) of a fluid medication such as insulin. According to one embodiment of the disclosure, a sterile cleansing swab 14 is configured for integration with one of the internal components of the needle pen cap assembly 10. That is, the cleansing swab 14 may include an absorptive gauze 16 disposed internally of the needle pen cap assembly 10. In this way, a user may prepare an injection site without the need to purchase, store, and transport a sterile swab in addition to the other items associated with injecting a fluid medication.

In one embodiment, the cleansing swab 14 may be disposed in combination with another internal component of the needle cap assembly 10 including, (i) a needle cap 22 having a needle cannula 22N disposed through a web portion of the needle cap 22, (ii) an internal cap 24 configured to cover an injection end 25 of the needle cannula 22N, (iii) an external cap 26 configured to envelope the needle and internal caps 22, 24, and a (iv) sealing tab 28 configured to seal a cavity 34 of the external cap 26. In the described embodiment, the cleansing swab 14 includes an absorptive gauze 16, which is loaded/doped with the cleansing fluid, and adhesively-bonded to an internal surface of the needle pen cap assembly 10. In this embodiment, the cleansing swab 14 may be disposed in combination with an underside surface of the sealing tab 28. That is, since the sealing tab 28 produces a vapor-locked cavity 34 upon being sealed against the rim flange 38 of the external cap 26, the cleansing fluid will be protected from drying air and not evaporate from the loaded gauze 14.

In another embodiment, the cleansing swab 14 may be sealed within a self-contained impervious packet 40, and bonded to the underside surface of the sealing tab 28. By sealing the self-contained impervious packet 40 internally of the needle pen cap 22, the absorptive gauze 16 is redundantly protected, i.e., by the impervious packet 40 and the sealed needle cap assembly 10.

Figure 3:
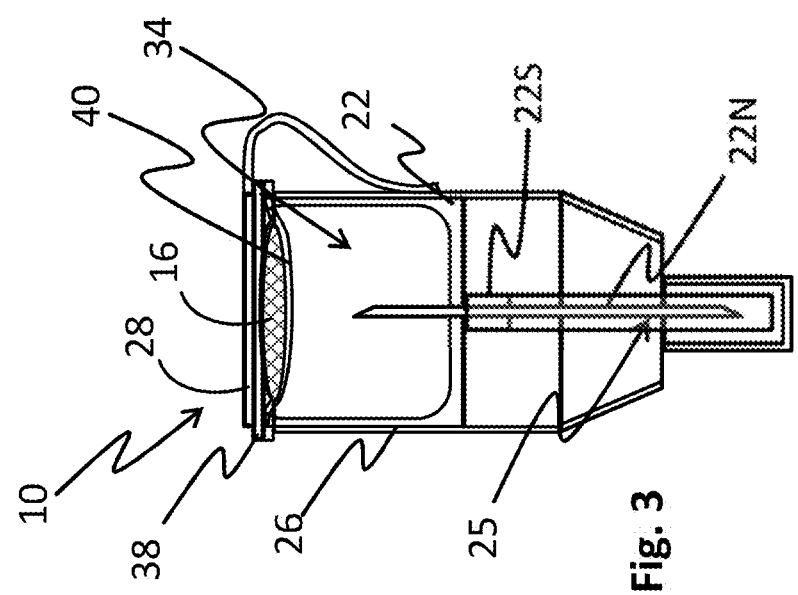
FIG. 3 depicts a sectioned side view of one embodiment of the needle pen cap assembly including a cleansing packet/swab disposed in combination with the underside surface of the sealing tab, which cleansing packet includes a cleansing swab loaded with a cleansing fluid and is enclosed within its own sealing packet to prevent evaporation of the cleaning fluid.

In FIG. 3, a partially-sectioned needle pen cap assembly 10 is depicted wherein the needle cap 22 supports a needle cannula 22N, i.e., through a web portion of the needle cap 22. An internal cap 24 is configured to cover an injection end 25 of the needle cannula 24, frictionally engaging a stub shaft portion 22S of the needle cap 22. An external cap 26 defines an internal cavity 34 for receiving the needle and internal caps 22, 24 of the needle cap assembly 10. Finally, the loaded cleansing swab 14 is configured to be adhesively-bonded to the underside surface of a sealing tab 30.

Operationally, and referring to FIGS. 4, 5 and 6, a user pulls the sealing tab 30 from a rim flange 38 of the external cap 26. This step exposes the sealed packet 40 containing the cleansing swab 14 along the underside of the tab 30. The user opens the packet 40 to expose the cleansing swab 14 to ambient air such that the swab 14 is prepared for cleaning an injection site 42 (i.e., the region bounded by the dashed lines in FIGS. 5 and 6.) With the sealing tab 30 disposed between the thumb 44 and index/forefinger 48, the sealing tab 30 is displaced vigorously to cause the cleansing swab 14 to clean/wipe the injection site 42 of the needle pen 20. Upon being cleaned/sterilized by the gauze 16 of the cleansing swab 14, the needle cannula 22 of the needle pen 20 may be inserted into the injection site 42. That is, the user may inject the fluid medication into the injection site by depressing the plunger 50 of the needle pen 20 (see FIG. 2).

Figure 7:
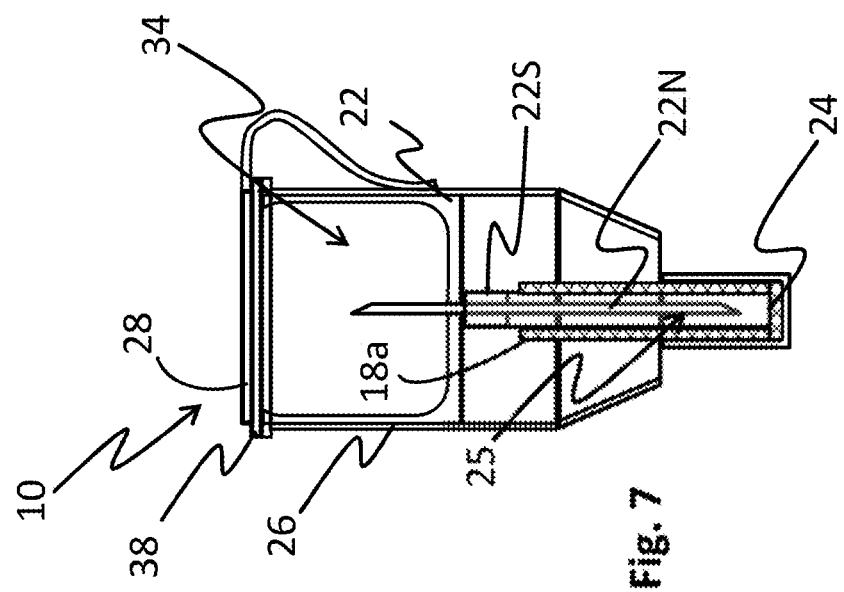
FIG. 7 depicts a sectioned side view of another embodiment of the needle pen cap assembly wherein a cleansing swab is disposed in combination with the internal cap of the needle cannula.

In another embodiment of the disclosure depicted in FIG. 7, a cleansing swab 18a is integrated with another internal element of the needle pen cap assembly 10. More specifically, the cleansing swab 18a may be integrated with the internal cap 24 which covers the injection end 22N of the needle cannula 22. In this embodiment, the cleansing swab 18a is wrapped around the cylindrically-shaped internal cap 24 and separated from the needle cap 22 to wipe/clean the injection site 42.

In another embodiment of the disclosure depicted in FIGS. 8 and 9, a cleansing swab 18b may be disposed over the external cap 52 of the needle cap. More specifically, a sealing member 54 may be disposed over the cleansing swab 18b to form a fluid tight seal with an intermediate or conical portion 56 of the needle pen cap assembly 10. For example, a shrink wrap membrane 54 may be disposed over the cleansing swab and sealed to the conical portion 56 of the needle pen cap assembly 10.

Figure 10:
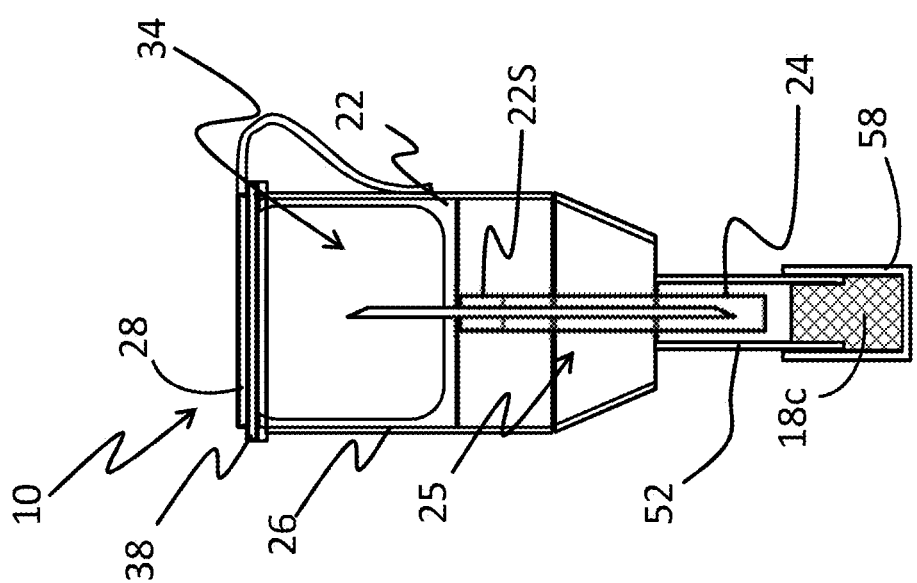
FIG. 10 depicts a sectioned side view of yet another embodiment of the needle pen cap assembly wherein a cleansing swab is disposed in combination with the end cap of the needle pen cap assembly and a sealing cap is disposed over the cleansing swab to form a fluid tight seal with the peripheral surface of the end cap.

In yet another embodiment shown in FIG. 10, a cleansing swab 18c may be formed similar to an eraser tip such that a smaller diameter portion fits within an open end of the external cap 52. A sealing cap 58 is disposed over the cleansing swab 18c and sealed to the external peripheral surface of the external cap 52. In another embodiment, not shown, a packet containing a cleansing swab may be simply be placed into the external cap 26 and closed by sealing the tab 28 to the rim-flange 38 of the external cap 26. All of the embodiments disclosed are contained within the vapor-locked cavity 34 of the external cap 26, which is sealed by the tab 28.

In summary, a cleansing swab or gauze 14, 16, 18 is placed internally of the needle cap assembly. The cleansing swab may be disposed in combination with any of the individual components of the needle cap assembly 10 provided that the component provides a liquid or moisture tight seal with other components of the needle cap assembly 10. As such the cleansing swab or gauze 14, 16, 18 is sealed within the needle cap assembly 10 and replaces the need to carry separate alcohol swabs or a cotton balls moistened with alcohol. That is a separate container of alcohol, absorptive gauze and/or cotton balls need not be carried inasmuch as the cleansing swab 14 is integrated with an element or component of the needle cap assembly 10.

To the extent that the claims recite the phrase "at least one of" in reference to a plurality of elements, this is intended to mean at least one or more of the listed elements, and is not limited to at least one of each element. For example, "at least one of an element A, element B, and element C," is intended to indicate element A alone, or element B alone, or element C alone, or any combination thereof. "At least one of element A, element B, and element C" is not intended to be limited to at least one of an element A, at least one of an element B, and at least one of an element C.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A needle cap assembly comprising:
   a needle cap having a needle cannula for subcutaneous injection of a fluid medication into an injection site, and outwardly-facing injection end and an inwardly-facing syringe end configured to be integrated with a needle pen assembly;
   an internal needle cap configured to cover the injection end of the needle cap;
   an external needle cap which envelops the internal needle cap and the needle cap, the external cap defining a sealing surface along an opening of the cavity;
   the external cap including an open end portion and a sealing cap disposed over the open end portion defining a second cavity;
   a tab having an adhesive disposed along one side thereof and defining a peripheral edge, the adhesive operative to seal the peripheral edge to the sealing surface of the external; and
   a cleansing swab having an absorptive material loaded with a cleaning fluid and disposed internally of the second cavity defined by the external cap and the sealing cap, the cleansing swab attached to an end portion of the internal needle cap and separated therefrom so as to provide a gap between the cleansing swab and the injection end of the needle cap and, furthermore, covered by the external cap and the sealing cap; the sealing cap enveloping and in contact with both an end portion of the external cap and the cleansing swab;
   wherein the tab and the sealing cap seal the needle cap, internal needle cap and the cleansing swab within the cavity of the external cap so as to mitigate evaporation of the fluid medication from the cleansing swab; and
   where in the sealing cap is detached from the external cap to: (i) expose the internal needle cap and (ii) permit cleaning of the injection site by the cleansing swab prior to injection of the fluid medication by the needle pen assembly; and
   when the external cap is detached from the needle cannula to remove the cleansing swab and expose the internal needle cap.

2. The needle cap assembly of claim 1 wherein the cleansing swab is contained within an impervious membrane to prevent evaporation of the cleansing fluid.

3. The needle cap assembly of claim 2 wherein the impervious membrane is a shrink wrap membrane disposed over the cleansing swab to prevent evaporation of the cleansing fluid.

* * * * *

UNITED STATES PATENT AND TRADEMARK OFFICE
CERTIFICATE OF CORRECTION

PATENT NO. : 11,253,687 B2
APPLICATION NO. : 16/035149
DATED : February 22, 2022
INVENTOR(S) : Michael J. Gilman It is certified that error appears in the above-identified patent and that said Letters Patent is hereby corrected as shown below:

On the Title Page

Column 2, ABSTRACT:
Change "cleansing swab disposed in internally of the needle cap" to --cleansing swab disposed internally of the needle cap--

In the Specification

Column 2, Line 19:
Change "to those parts to be indicated with different numerals." to --those parts to be indicated with different numerals.--

Column 2, Line 27:
Change "of the needle cannula, an external cap configured to envelope" to --of the needle cannula, an external cap configured to envelop--

Column 2, Line 48:
Change "FIG. 5 depicts a partially secion side view of the sealing" to --FIG. 5 depicts a partially sectioned side view of the sealing--

Column 3, Line 16:
Change "assembly, and (v) a cleansing swab disposed in internally of the" to --assembly, and (v) a cleansing swab disposed internally of the--

Column 3, Line 5:
Change "(iii) an external cap 26 configured to envelope the needle and" to --(iii) an external cap 26 configured to envelop the needle and--

Signed and Sealed this
Thirteenth Day of September, 2022

*Katherine Kelly Vidal*
Katherine Kelly Vidal
*Director of the United States Patent and Trademark Office*

CERTIFICATE OF CORRECTION (continued)
U.S. Pat. No. 11,253,687 B2

Column 4, Line 62:
Change "shown, a packet containing a cleansing swab may be simply" to --shown, a packet containing a cleansing swab may simply--

Column 5, Line 9:
Change "carry separate alcohol swabs or a cotton balls moistened" to --carry separate alcohol swabs or cotton balls moistened--

In the Claims

Claim 15, Column 6, Line 12:
Change "external; and" to --external cap; and--

Claim 15, Column 6, Line 32:
Change "when the external cap is detached from the needle cannula" to --wherein the external cap is detached from the needle cannula--